(12) United States Patent
Jung et al.

(10) Patent No.: US 8,411,277 B2
(45) Date of Patent: Apr. 2, 2013

(54) METHOD AND APPARATUS FOR CONTROLLING QUALITY OF A MICROFLUIDIC DEVICE

(75) Inventors: Won-jong Jung, Seongnam-si (KR); Jae-young Kim, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 385 days.

(21) Appl. No.: 12/765,956

(22) Filed: Apr. 23, 2010

(65) Prior Publication Data

US 2011/0096331 A1    Apr. 28, 2011

(30) Foreign Application Priority Data

Oct. 27, 2009   (KR) ................ 10-2009-0102287

(51) Int. Cl.
   *G01N 21/84*    (2006.01)
   *G01N 21/55*    (2006.01)

(52) U.S. Cl. ........................... 356/448; 356/246

(58) Field of Classification Search .......... 356/445, 356/435, 440, 246, 448; 250/559.29, 559.4; 137/828, 807, 833, 67, 13; 435/4, 6, 7.1, 435/69.2, 91.1, 278.2, 288.5; 422/68.1, 103, 422/130

See application file for complete search history.

(56) References Cited

U.S. PATENT DOCUMENTS

| | | | |
|---|---|---|---|
| 6,182,941 B1 | 2/2001 | Scheurenbrand et al. | |
| 6,319,469 B1* | 11/2001 | Mian et al. | 422/64 |
| 6,731,387 B2* | 5/2004 | Neimark et al. | 356/435 |
| 6,767,706 B2* | 7/2004 | Quake et al. | 435/6.13 |
| 7,023,007 B2* | 4/2006 | Gallagher | 250/559.29 |
| 7,159,618 B2* | 1/2007 | Broyer et al. | 137/828 |
| 7,285,420 B2* | 10/2007 | Fontaine et al. | 436/164 |
| 7,583,853 B2* | 9/2009 | Taylor et al. | 382/276 |
| 7,897,330 B2* | 3/2011 | Patel et al. | 435/4 |
| 2004/0148777 A1* | 8/2004 | Sjolander et al. | 29/890.127 |
| 2005/0109396 A1* | 5/2005 | Zucchelli et al. | 137/67 |
| 2006/0073484 A1* | 4/2006 | Mathies et al. | 435/6 |
| 2008/0041453 A1* | 2/2008 | Wimberger-Friedl | 137/13 |
| 2010/0233792 A1* | 9/2010 | Begley et al. | 435/287.1 |

FOREIGN PATENT DOCUMENTS

| | | |
|---|---|---|
| JP | 11-040821 A | 2/1999 |
| JP | 2004-340702 A | 12/2004 |
| JP | 2005-130642 A | 5/2005 |

* cited by examiner

*Primary Examiner* — Sang Nguyen

(57) ABSTRACT

A method for determining the quality of a microfluidic device, the method including placing a microfluidic device including a valve on a stage; radiating light on the valve of the microfluidic device; detecting light reflected from the valve using a photodetector; opening the valve of the microfluidic device; and comparing a change of the light reflected from the valve when the valve is opened with previously-stored reference data to evaluate a quality of the microfluidic device, wherein the valve of the microfluidic device includes a valve seat, which protrudes into a microfluidic path, and a polymer film, which opens and closes the valve.

25 Claims, 5 Drawing Sheets

14 17 15 16

55

56

METHOD AND APPARATUS FOR CONTROLLING QUALITY OF A MICROFLUIDIC DEVICE

CROSS-REFERENCE TO RELATED APPLICATIONS

This application claims priority to Korean Patent Application No. 10-2009-0102287, filed on Oct. 27, 2009, and all the benefits accruing therefrom under 35 U.S.C. §119, the content of which in its entirety is herein incorporated by reference.

BACKGROUND

1. Field

The present disclosure relates to a method and apparatus for controlling the quality of a microfluidic device.

2. Description of the Related Art

Clinical or environment-related sample analyses are performed using a series of bio-chemical, chemical, and mechanical processes. Recently, technologies for detecting or monitoring biological samples have greatly improved. In particular, a nucleic acid-based method of molecular detection has high accuracy and sensitivity and has been increasingly used in various fields such as infectious diseases, cancer diagnosis, medicine genomics, and new medicine development.

Microfluidic devices are widely used to analyze samples conveniently and accurately for various purposes. A microfluidic device may include a plurality of sample inlets, a plurality of sample outlets, a plurality of microfluidic channels, and a plurality of reaction chambers, which are disposed on a thin substrate to conveniently carry out various tests on a sample. Also, the microfluidic device may further include a microfluidic valve disposed in a microfluidic channel via which a sample and a reagent are placed in a desired position. The microfluidic valve is generally formed of a polymer thin film. When the microfluidic device is manufactured, the operating state and the quality of the microfluidic valve are desirably determined.

SUMMARY

Provided is a method of controlling the quality of a microfluidic device by detecting the operating state of a valve, which includes a polymer film, by using a change of optical characteristics thereof.

Also provided is an apparatus for controlling the quality of a microfluidic device by detecting the operating state of a valve, which includes a polymer film, by using a change of optical characteristics thereof.

Additional aspects will be set forth in part in the description which follows and, in part, will be apparent from the description.

According to an aspect of a method of determining the quality of a microfluidic device, the method includes placing a microfluidic device including a valve on a stage; radiating light on the valve of the microfluidic device; detecting light reflected from the valve using a photodetector; opening the valve of the microfluidic device; and comparing a change of light reflected from the valve when the valve is opened with previously-stored reference data to evaluate a quality of the microfluidic device, wherein the valve of the microfluidic device includes a valve seat, which protrudes into a microfluidic path, and a polymer film, which opens and closes the valve.

For example, the change of the light reflected from the valve, which occurs when the valve is opened, may include a shaded region which occurs when the polymer film contacts a substrate of the microfluidic device, a Newton's ring which occurs around the shaded region, a change of brightness of an edge of a surface of the valve seat, or a combination thereof.

In an embodiment, a diameter of the shaded region is greatest when the valve is fully open.

In an embodiment, a shaded region does not occur at the edge of the surface of the valve seat when the valve is closed, and the shaded region occurs at the edge of the surface of the valve seat when the valve is open.

Furthermore, the previously-stored reference data may be statistically determined by measuring a change of light reflected from a reference valve when the reference valve is opened.

The reference data may include an average size of the shaded region and a tolerance of the size of the shaded region, the tolerance including an upper limit value and a lower limit value of the size of the shaded region of the reference valve.

The valve or reference valve may be opened by applying a vacuum to a space defined by the polymer film and the substrate of the microfluidic device.

In an embodiment, the reference data may further include a change of a shape of the shaded region, a change of a shape of a Newton's ring in response to a vacuum applied to the space, or a combination thereof.

Furthermore, the reference data may further include data about an image formed by light reflected from the reference valve before the vacuum is applied to the space.

In an embodiment of the method, after the quality of the microfluidic device is evaluated based on the valve, the quality of the microfluidic device is further evaluated based on another valve of the microfluidic device by sequentially moving the microfluidic device to position the other valve of the microfluidic device at a selected location.

According to another aspect of an apparatus for determining the quality of a microfluidic device, the apparatus includes a stage on which a microfluidic device including a valve is placed; a light source, which for radiates light on the valve of the microfluidic device; a photodetector, which detects light reflected from the valve; and a controller, which compares a change of the light reflected from the valve when the valve is opened with previously-stored reference data to determine a quality of the microfluidic device.

The light source may be a laser diode ("LD") or a light emitting diode ("LED"), each of which emits light having a single wavelength, or a white light source, which emits white light.

In an embodiment, the photodetector is one of a photodiode array, which detects a two-dimensional image, a charge coupled device ("CCD"), or a complementary metal semiconductor ("CMOS") device.

The apparatus may further include a first lens unit, which changes light incident on the microfluidic device into parallel light, and a second lens unit, which changes light incident on the photodetector into parallel light.

A reflective metal coating or a diffraction pattern may be disposed on a surface of the stage or disposed on an outer surface of the microfluidic device.

The valve of the microfluidic device may include a valve seat, which protrudes into a microfluidic path, and a polymer film, which opens and closes the valve.

Furthermore, the stage may include an XY-stage, which moves along two substantially perpendicular axes.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
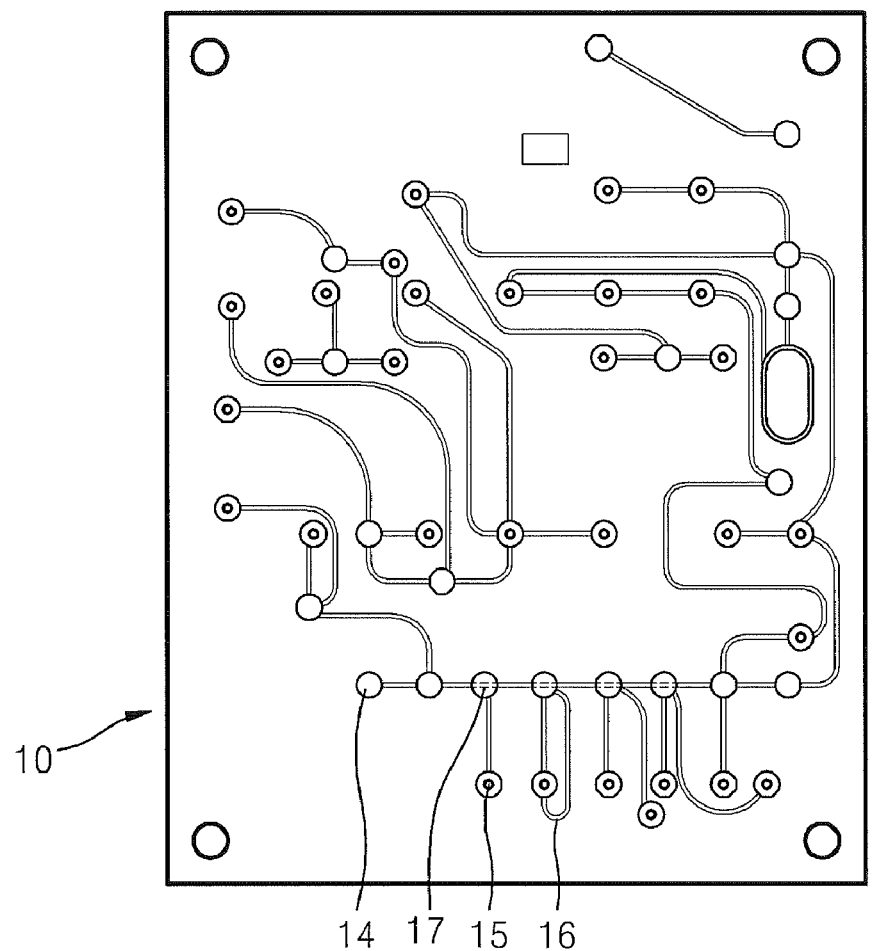
FIG. 1 is a schematic plan view of an exemplary embodiment of a microfluidic device.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Like reference numerals refer to like elements throughout. It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers, and/or sections should not be limited by these terms. These terms are only used to distinguish one element, component, region, layer, or section from another element, component, region, layer or section. Thus, a first element, component, region, layer, or section discussed below could be termed a second element, component, region, layer, or section without departing from the teachings of the present invention.

The terminology used herein is for the purpose of describing particular embodiments only and is not intended to be limiting. As used herein, the singular forms "a," "an," and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

FIG. 1 is a schematic plan view of an exemplary embodiment of a microfluidic device 10. Referring to FIG. 1, the microfluidic device 10 includes a hole 15 through which a sample or air may flow in or out, a reaction chamber 14, in which a chemical or biological reaction of the sample may occur, a microfluidic channel 16 via which the sample is moved, and a microfluidic valve 17, which controls the sample such that it may flow in a desired direction or to a desired position. The hole 15 may be a hole through which only the sample flows in or out, or the hole may be a hole through which only air, which controls the microfluidic valve 17, flows in or out. The microfluidic valve 17 is disposed in the microfluidic channel 16 and may allow or block flow of the sample through the microfluidic channel 16.

Figure 2:
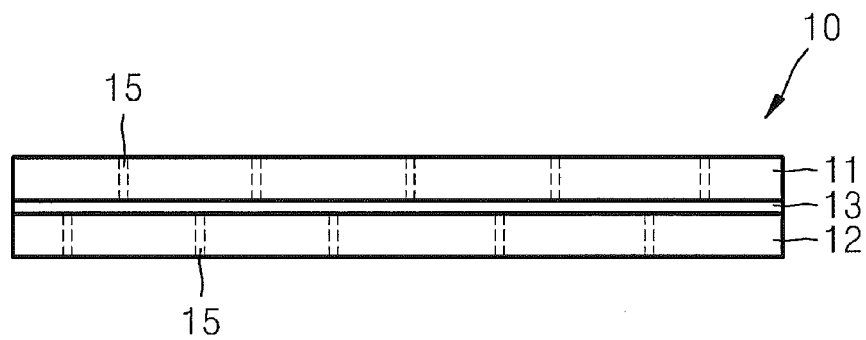
FIG. 2 is a schematic cross-sectional view of an exemplary embodiment of the microfluidic device of FIG. 1.

The microfluidic valve 17 may comprise a polymer film 13. FIG. 2 is a schematic cross-sectional view of the microfluidic device 10 of FIG. 1, wherein in the microfluidic device 10 the microfluidic valve 17 is disposed in the microfluidic channel 16. Referring to FIG. 2, the microfluidic device 10 may include a first substrate 11 and a second substrate 12, and the polymer film 13 disposed between the first substrate 11 and the second substrate 12. The first and second substrates 11 and 12 are transparent. Although only the hole 15 is shown in FIG. 2, the microfluidic channel 16 (e.g. microfluidic paths) may be disposed in the first substrate 1 and the second substrate 12.

Figure 3:
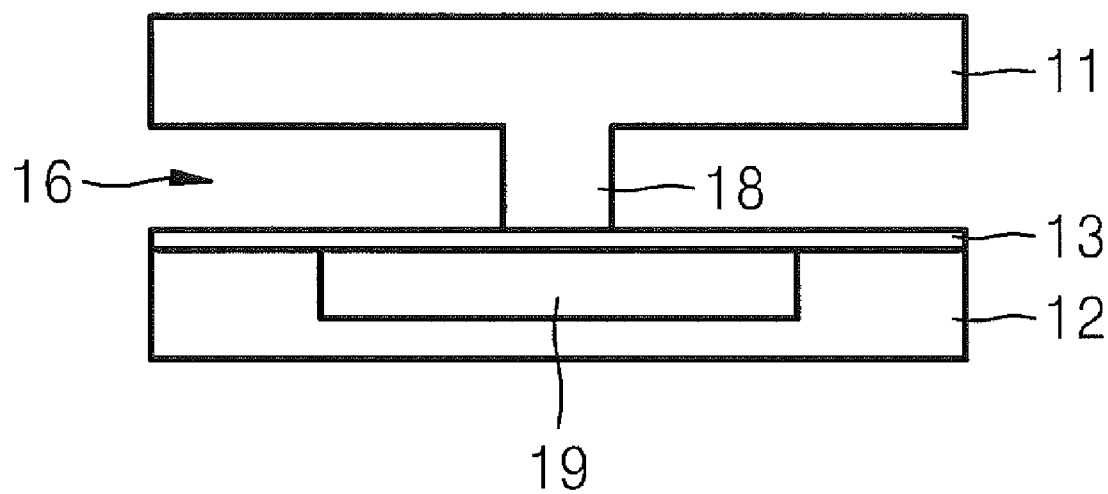
FIG. 3 is a cross-sectional view of an exemplary embodiment of a microfluidic valve disposed in the microfluidic device of FIG. 1.
Figure 4:
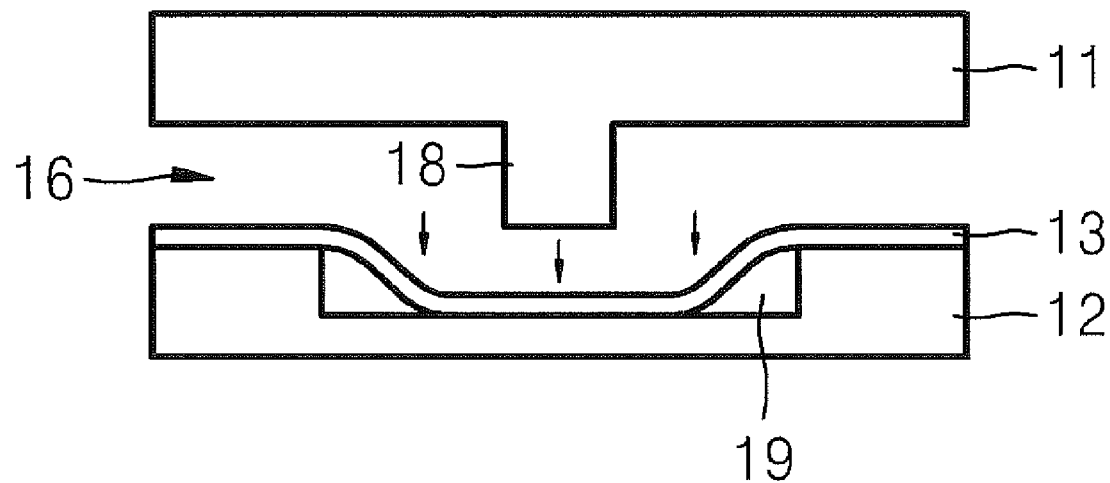
FIG. 4 is a schematic cross-sectional view of an exemplary embodiment of a normal opening operation of the microfluidic valve of FIG. 3.

FIG. 3 is a cross-sectional view of the microfluidic valve 17, which may be disposed in the microfluidic channel 16 of the microfluidic device 10 of FIG. 1, and FIG. 4 is a schematic cross-sectional view for explaining a normal opening operation of the microfluidic valve of FIG. 3

Referring to FIG. 3, a valve seat 18 protrudes into the microfluidic channel 16, which is disposed in the first substrate 11. Also, a space 19, which is defined by the polymer film and the second substrate, may be formed in the second substrate 12 by etching an area of the second substrate 12 corresponding to the valve seat 18. The space 19 and the valve seat 18 are separated from each other by the polymer film 13, which is disposed between the first substrate 11 and the second substrate 12, and the valve seat 18 may contact the polymer film 13. The microfluidic channel 16 may be connected to the hole 15 through which the sample flows in or out, and the space 19 may be connected to the hole 15 through which air flows in or out.

In the microfluidic valve 17 of FIG. 3, when a sufficient vacuum is applied to the space 19 the polymer film 13 is pulled toward the space 19 so that the microfluidic channel 16 may be opened, as illustrated in FIG. 4. Vacuum may be applied to the space 19 via the hole 15 disposed in the second substrate 12, for example. If the vacuum applied to the space 19 is sufficiently large, the polymer film 13 and the second substrate 12 contact each other, and thus the microfluidic valve 17 is fully opened. Then, for example, the sample that flows in via the hole 15 disposed in the first substrate 11 passes through the microfluidic valve 17 in the microfluidic channel 16 and flows in a desired direction (e.g., to a desired position). Alternatively, if the air pressure is applied to the space 19, the polymer film 13 is pushed toward the valve seat 18 so that the microfluidic channel 16 may be closed. Accordingly, the air pressure may be applied to the space 19 via the hole 15 disposed in the second substrate 12, for example. In an embodiment, the polymer film 13 contacts the surface of the valve seat 18, as illustrated in FIG. 3. As such, the flow of the sample may be substantially or entirely stopped.

The microfluidic device 10 having the above structure may be manufactured by bonding two substrates, i.e., the first substrate 11 and the second substrate 12. Thus, the first and second substrates 11 and 12 are desirably accurately aligned with respect to each other when the microfluidic device 10 is manufactured. When the first and second substrates 11 and 12 are not accurately aligned with respect to each other, the microfluidic valve 17 may not operate normally. Also, the sample may not stably flow in the microfluidic channel 16, and a leakage (e.g., water leakage) may occur. Thus, after the microfluidic device 10 is manufactured, it is desirable to determine if the microfluidic device 10 is defective by checking in real-time, whether, for example, the microfluidic valve 17 operates normally.

Figure 5:
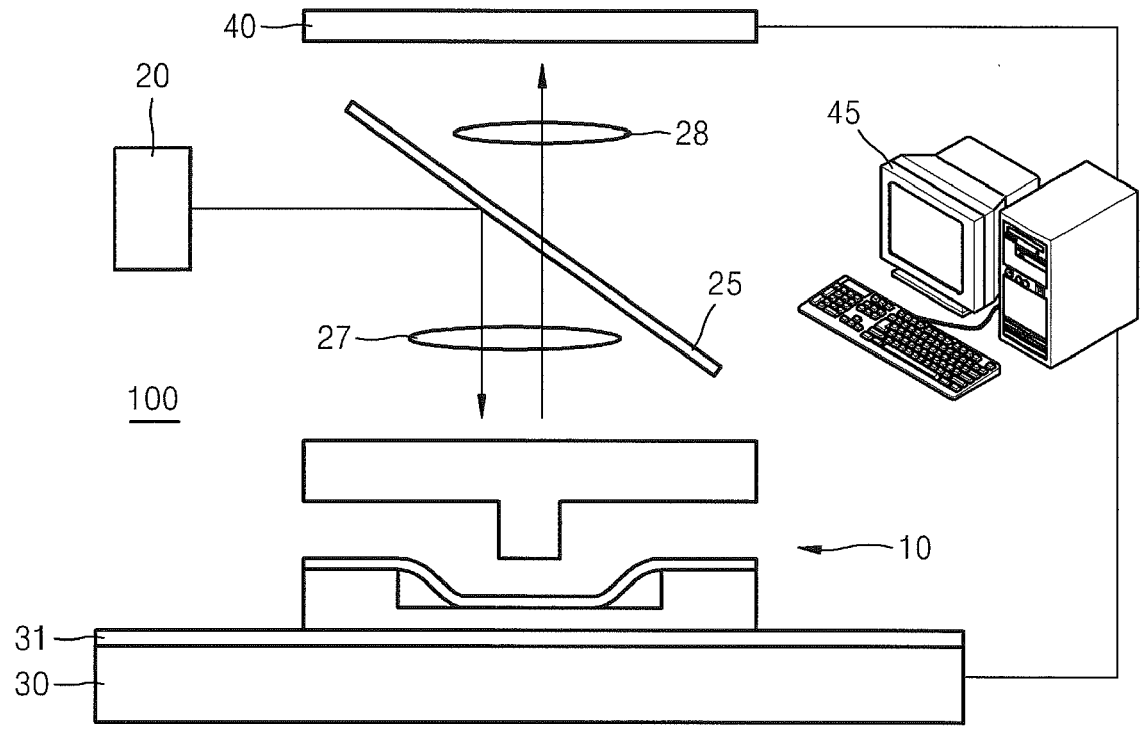
FIG. 5 schematically shows an apparatus for controlling (e.g., determining) the quality of the microfluidic device of FIG. 1 by checking in real-time whether the microfluidic valve of FIG. 3 of the microfluidic device of FIG. 1 operates normally.

FIG. 5 schematically shows an apparatus 100 for controlling (e.g., determining) the quality of the microfluidic device 10 of FIG. 1 by checking in real-time whether the microfluidic valve 17 of FIG. 3 of the microfluidic device 10 of FIG. 1 operates normally. Referring to FIG. 5, the apparatus 100 for controlling the quality of the microfluidic device 10 of FIG. 1 may include a stage 30 on which the microfluidic device 10 to be tested is placed, a light source 20, which emits light to be radiated on the microfluidic device 10, a photodetector 40, which detects light reflected by the microfluidic device 10, and a controller 45, which controls the stage 30, the light source 20, and the photodetector 40. The light source 20 may be a laser light source such as a laser diode ("LD") or a light emitting diode ("LED") which emit light having a single wavelength, or a white light source which emits white light. The photodetector 40 may be a photodiode array or a solid state imaging device, such as a charge coupled device ("CCD") or a complementary metal semiconductor ("CMOS") device. Also, the controller 45 may be a general computer device including software which analyzes an image provided by the photodetector 40, for example.

The apparatus 100 of FIG. 5 may further include a first lens unit 27 which changes light incident on the microfluidic device 10 into parallel light, and a second lens unit 28 which changes light incident on the photodetector 40 into parallel light. When the light source 20 is disposed to be perpendicular to an optical path between the microfluidic device 10 and the photodetector 40, a semi-transmission plate 25 may be additionally disposed on the optical path between the microfluidic device 10 and the photodetector 40. The semi-transmission plate 25 may reflect light generated in the light source 20 from the microfluidic device 10 and transmit light reflected from the microfluidic device 10 to the photodetector 40. In another embodiment, the light source 20 may be placed in the same position as the photodetector 40 or at an opposite side to the photodetector 40, e.g., below the stage 30, according to different designs of the apparatus 100 of FIG. 5. In an embodiment, the semi-transmission plate 25 may be omitted.

Figure 6:
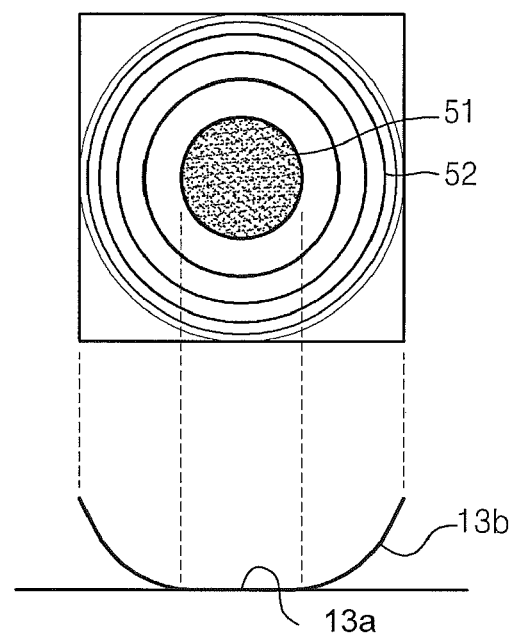
FIG. 6 schematically shows an exemplary embodiment of a shaded region and a diffraction pattern formed in an image observed via the apparatus for controlling the quality of the microfluidic device of FIG. 5.

The apparatus 100 of FIG. 5 may determine whether the microfluidic valve 17 operates normally by detecting a change of optical characteristics which occurs when the microfluidic valve 17 of the microfluidic device 10 operate. FIG. 6 illustrates the principle of the apparatus 100 of FIG. 5 and schematically shows a shaded region 51 and a diffraction pattern formed in an image observed via the apparatus 100 of FIG. 5.

First, when the microfluidic valve 17 is closed, as illustrated in FIG. 3, the polymer film 13 is in a substantially flat state. When the polymer film is flat, when light is radiated on the microfluidic device 10, a pattern is not formed in an image formed by light reflected from the microfluidic device 10. However, when the microfluidic valve 17 is opened while light is radiated (e.g., continuously radiated) on the microfluidic device 10, as illustrated in FIG. 4, a pattern, which is shown in the upper portion of FIG. 6, is formed by the reflected light. In other words, referring to FIG. 6, the polymer film 13 is pulled due to the vacuum and contacts the second substrate 12. In an embodiment, a contact portion 13a, in which the polymer film 13 and the second substrate 12 contact each other, is a substantially circular region having a selected width. The amount of light reflection is reduced in the circular contact portion 13a and thus the circular shaded region 51, which is shown in FIG. 6, occurs.

Also, the polymer film 13 is bent (e.g. deflected) with a selected curvature in a circumferential portion 13b of the contact portion 13a. Then, a path difference between light reflected from the polymer film 13 and light reflected from the second substrate 12 or the stage 30 under the polymer film 13 occurs. The path difference increases in proportion to a radial direction from a central portion of the microfluidic valve 17. Thus, interference between the light reflected from the polymer film 13 and the light reflected from the second substrate 12 or the stage 30 under the polymer film 13 occurs. An interference pattern formed in this way is referred to as a Newton's ring 52. As illustrated in FIG. 6, the inference pattern of the Newton's ring 52 formed in a circumferential portion of the shaded region 51 may appear in the form of a substantially concentric circle.

Thus, the controller 45 of the apparatus 100 of FIG. 5 may check whether the microfluidic valve 17 is sufficiently opened by analyzing the shape and size of the shaded region 51 and the Newton's ring 52 which occurs when the microfluidic valve 17 is opened. The microfluidic device 10 may comprise a transparent material, and thus the shaded region 51 and the Newton's ring 52 may have low intensity and be difficult to observe. Accordingly, in an embodiment, to more accurately observe the shaded region 51 and the Newton's ring 52, an optical coating 31 may optionally be disposed on the surface of the stage 30, as illustrated in FIG. 5. For example, the optical coating 31, which is optionally disposed on the surface of the stage 30, may comprise a reflective metal coating which enhances reflection. The metal coating may comprise a metal having excellent reflection such as chromium (Cr). Also, instead of using a metal coating as the optical coating 31, the diffraction pattern may be used in order to reinforce the interference patterns. FIG. 5 illustrates an embodiment wherein the optical coating 31 is disposed on the surface of the stage 30. In another embodiment, the optical coating 31 may be disposed on an outer surface of the first substrate 11 of the microfluidic device 10, for example.

In an embodiment, in order to establish a basis for determining whether the microfluidic device 10 operates normally, data about the microfluidic device 10, i.e., information about the shape and size of the shaded region 51 and the Newton's ring 52, may be measured and stored in advance. To this end, the vacuum at which the microfluidic valve 17 of the microfluidic device 10 is fully open and the shape and size of the shaded region 51 and the Newton's ring are desirably measured in advance while varying the vacuum applied to the space 19 defined by the second substrate 12.

Figure 7A:
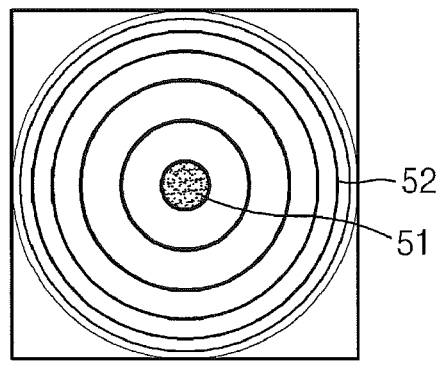
FIGS. 7A through 7C schematically shows a change of a shaded region and a diffraction pattern according to a change of an area where a polymer film of the microfluidic valve of FIG. 3 contacts a substrate of the microfluidic device of FIG. 1.
Figure 7B:
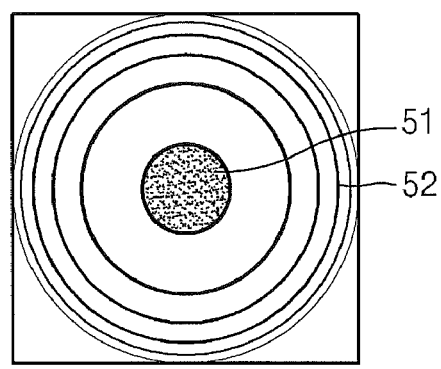
Figure 7C:
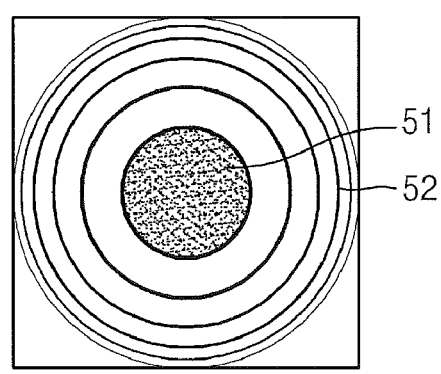

FIGS. 7A through 7C schematically show a change of the shaded region 51 and the Newton's ring 52, which occur according to a change of an area in which a polymer film of the microfluidic valve 17 of FIG. 3 contacts the second substrate 12 of the microfluidic device 10 of FIG. 1, according to a change of the intensity of the pressure applied to the space 19. Referring to FIGS. 7A through 7C, as the pressure applied to the space 19 is increased, the diameter of the shaded region 51 gradually increases, and the size of the Newton's ring 52 gradually decreases. Thus, when the microfluidic valve 17 is fully open, the diameter of the shaded region 51 also has the greatest value. For example, in an embodiment wherein the polymer film 13 is in a fully open at the greatest degree at a pressure of about 1 kilopascals (kPa) to about 500 kPa, specifically about 5 kPa to about 250 kPa, more specifically about 80 kPa, the controller 45 may measure information about the diameter of the shaded region 51, the diameter of the Newton's ring 52, and the number of diffraction patterns of the Newton's ring 52 in the state shown in FIG. 7C, and store the information in an information recording device (not shown). Also, the controller 45 may store an image as shown in FIG. 7C in the information recording device. As another example, the controller 45 may analyze a change of the shaded region 51 and the Newton's ring 52 according to the change of the intensity of the vacuum of FIGS. 7A through 7C and store data of analysis in the information recording device. The information recording device may be disposed in the controller 45, and may be a hard disk drive ("HDD"), for example.

Information and the image stored in the information recording device of the controller 45 may be a basis for testing the quality of the microfluidic device 10 which is to be actually manufactured in a mass production process. In an embodiment, basic data may be statistically determined and provided in advance by measurement of a reference microfluidic device. For example, an average size of the shaded region 51 of a plurality of shaded regions, and a tolerance of the size of the shaded region, the tolerance including an upper limit value and a lower limit value of the reference microfluidic device, may be measured in advance.

Then, the controller 45 may compare an image formed by reflected light, which is obtained by radiating light on the microfluidic device 10, i.e., the shaded region 51 and the Newton's ring 52, with previously-stored reference data, and determine whether the microfluidic device 10 is defective. For example, a vacuum of about 1 kPa to about 500 kPa, specifically about 5 kPa to about 250 kPa, more specifically about 80 kPa may be applied to the space 19 of the microfluidic device 10, and the size of the shaded region 51 may be measured. When the size of the shaded region 51 is different from the size of the previously-stored reference data, in particular, when the size of the shaded region 51 is smaller than the lower limit value or greater than the upper limit value and is not within the range of the tolerance, the controller 45 may determine that the microfluidic device 10 is defective. More specifically, for example, as illustrated in FIGS. 7A through 7C, a change of the shape of the shaded region 51 and the Newton's ring 52 according to the vacuum applied to the space 19 may be compared with the previously-stored reference data while varying the vacuum pressure applied to the space 19, and it may be determined whether the microfluidic device 10 is defective or non-defective. Also, an image formed by the light reflected from the microfluidic valve 17 and statistical data about the image may be stored in advance in the information recording device of the controller 45 before the vacuum applied is applied to the space 19. Accordingly it may be determined whether the state of the microfluidic valve 17 of the microfluidic device 10, which may be manufactured in a mass production process, is good or not before the vacuum is applied to the space 19.

Figure 8A:
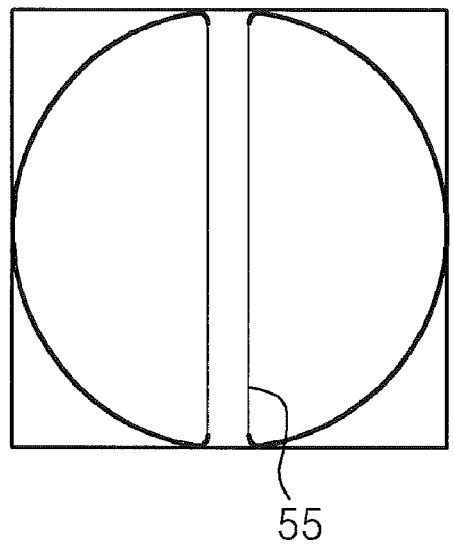
FIGS. 8A and 8B schematically shows a change of brightness of an edge of a valve seat when the polymer film of the microfluidic valve of FIG. 3 contacts the surface of the valve seat and when the polymer film of the microfluidic valve of FIG. 3 is detached from the surface of the valve seat, respectively.
Figure 8B:
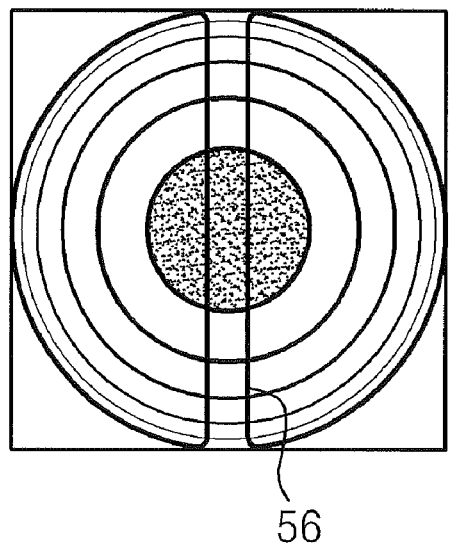

Also, in another embodiment of the method of evaluating the quality of the microfluidic device 10 of FIG. 1, a change of brightness of an edge of a valve seat 18 may be observed. FIGS. 8A and 8B schematically shows a change of brightness of an edge of the valve seat 18 when the polymer film 13 of the microfluidic valve 17 of FIG. 3 contacts the surface of the valve seat 18 and when the polymer film 13 of the microfluidic valve 17 of FIG. 3 is detached from the surface of the valve seat 18, respectively. For example, when a vacuum is not applied to the space 19 and the polymer film 13 contacts the surface of the valve seat 18, i.e., when the microfluidic valve 17 is closed, an edge portion 55 of the valve seat 18 is not well formed (e.g., defined), as illustrated in FIG. 8A. However, when the vacuum is applied to the space 19 and the polymer film 13 is detached from the surface of the valve seat 18, i.e., when the microfluidic valve 17 is open, a shaded region 56 occurs in the edge portion 55 of the valve seat 18, as illustrated in FIG. 8B. Thus, the controller 45 may check whether the change of brightness occurs in the edge portion 55 of the valve seat 18 before and after the vacuum is applied to the space 19, and thus, it may be easily determined from the checking whether the microfluidic device 10 is defective or non-defective.

In an embodiment, a plurality of microfluidic valves are disposed (e.g., formed) in a microfluidic device 10. For example, 20 or more microfluidic valves may be disposed (e.g., formed) in a microfluidic device 10. The position of each microfluidic valve of the plurality of microfluidic valves may be stored in the controller 45 of the apparatus 100 of FIG. 5. Thus, the apparatus 100 of FIG. 5 may radiate light on the plurality of microfluidic valves while moving the stage to position each of the microfluidic valves 17 at a selected location and each microfluidic valve may be checked using the light reflected from the microfluidic valve 17 while the microfluidic valve 17 is opened and closed to determine whether each microfluidic valve 17 of the plurality of microfluidic valves operates normally. To this end, the stage 30 on which the microfluidic device 10 is placed may be an XY-stage that may move along two substantially perpendicular axes. In an embodiment, all processes of the microfluidic device 10 from its manufacture to testing may be performed automatically. Also, the microfluidic device 10 may have high reliability. Thus, uniformity in the quality of the microfluidic device 10, an increase in productivity, a reduction in a defect rate, a reduction in labor cost, and an improvement in an efficiency of production and process management may be achieved.

It should be understood that the exemplary embodiments described therein should be considered in a descriptive sense only and not for purposes of limitation. Descriptions of features or aspects within each embodiment should be considered as available for other similar features or aspects in other embodiments.

What is claimed is:

1. A method of determining the quality of a microfluidic device, the
   method comprising:
   placing a microfluidic device comprising a value on a stage;
   radiating light on the value of the microfluidic device;
   detecting light reflected from the valve using a photodetector;
   opening the valve of the microfluidic device; and
   comparing a change of the light reflected from the valve by a controller when the valve is opened with previously-stored reference data to evaluate a quality of the microfluidic device,
   wherein the valve of the microfluidic device comprises a valve seat, which protrudes into a microfluidic path, and a polymer film, which opens and closes the valve.

2. The method of claim 1, wherein the change of the light reflected from the valve, which occurs when the valve is opened, comprises a shaded region which occurs when the polymer film contacts a substrate of the microfluidic device, a Newton's ring which occurs around the shaded region, a change of brightness of an edge of a surface of the valve seat, or a combination thereof.

3. The method of claim 2, wherein a diameter of the shaded region is greatest when the valve is fully open.

4. The method of claim 2, wherein the shaded region does not occur at the edge of the surface of the valve seat when the valve is closed, and the shaded region occurs at the edge of the surface of the valve seat when the valve is open.

5. The method of claim 2, wherein the previously-stored reference data is statistically determined by measuring a change of light reflected from a reference valve when the reference valve is opened.

6. The method of claim 5, wherein the reference data comprises an average size of the shaded region and a tolerance of the size of the shaded region, the tolerance comprising an upper limit value and a lower limit value of the size of the shaded region of the reference valve.

7. The method of claim 5, wherein the valve or reference valve is opened by applying a vacuum to a space defined by the polymer film and the substrate of the microfluidic device.

8. The method of claim 7, wherein the reference data further comprises a change of a shape of the shaded region, a change of a shape of a Newton's ring in response to a vacuum applied to the space, or a combination thereof.

9. The method of claim 7, wherein the reference data further comprises data about an image formed by light reflected from the reference valve before the vacuum is applied to the space.

10. The method of claim 1, wherein after the quality of the microfluidic device is evaluated based on the valve, the quality of the microfluidic device is further evaluated based on another valve of the microfluidic device by sequentially moving the microfluidic device to position the other valve of the microfluidic device at a selected location.

11. An apparatus for determining the quality of a microfluidic device, the apparatus comprising:
    a stage on which a microfluidic device comprising a valve is placed;
    a light source positioned to radiate light on the valve of the microfluidic device;
    a photodetector positioned to detect light reflected from the valve; and
    a controller, which compares a change of the light reflected from the valve when the valve is opened with previously-stored reference data to determine a quality of the microfluidic device.

12. The apparatus of claim 11, wherein the light source is a laser diode or a light emitting diode, each of which emits light having a single wavelength, or a white light source, which emits white light.

13. The apparatus of claim 11, wherein the photodetector is one of a photodiode array, which detects a two-dimensional image, a charge coupled device, or a complementary metal semiconductor device.

14. The apparatus of claim 11, further comprising a first lens unit, which changes light incident on the microfluidic device into parallel light, and a second lens unit, which changes light incident on the photodetector into parallel light.

15. The apparatus claim 11, wherein a reflective metal coating or a diffraction pattern is disposed on a surface of the stage or is disposed on an outer surface of the microfluidic device.

16. The apparatus of claim 11, wherein the valve of the microfluidic device comprises a valve seat, which protrudes into a microfluidic path, and a polymer film, which opens and closes the valve.

17. The apparatus of claim 16, wherein the change of light reflected from the valve, when the valve is opened, comprises a shaded region which occurs when the polymer film contacts a substrate of the microfluidic device, a Newton's ring which occurs around the shaded region, a change of brightness of an edge of a surface of the valve seat, or a combination thereof.

18. The apparatus of claim 17, wherein a diameter of the shaded region is greatest when the valve is fully open.

19. The apparatus of claim 17, wherein a shaded region does not occur at an edge of the surface of the valve seat when the valve is closed, and a shaded region occurs at the edge of the surface of the valve seat when the valve is open.

20. The apparatus of claim 17, wherein the previously-stored reference data is statistically determined by measuring a change of the light reflected when a reference valve is opened.

21. The apparatus of claim 20, wherein the reference data further comprises an average size of the shaded region and a tolerance of the size of the shaded region, the tolerance comprising an upper limit value and a lower limit value of the size of the shaded region of the reference valve.

22. The apparatus of claim 20, wherein the valve or the reference valve is opened by applying a vacuum to a space defined by the polymer film and the substrate of the microfluidic device.

23. The apparatus of claim 22, wherein the reference data further comprises a change of a shape of shaded region, a change of a shape of a Newton's ring according to a vacuum applied to the space, or a combination thereof.

24. The apparatus of claim 22, wherein the reference data further comprises data about an image formed by light reflected from the reference valve before the vacuum is applied to the space.

25. The apparatus of claim 11, wherein the stage comprises an XY-stage, which moves along two substantially perpendicular axes.

* * * * *